United States Patent [19]

Demeter

[11] Patent Number: 4,997,435

[45] Date of Patent: Mar. 5, 1991

[54] PERCUTANEOUS CATHETER WITH ENCAPSULATING RECEPTACLE

[75] Inventor: Robert J. Demeter, Danville, Ind.

[73] Assignee: Methodist Hospital of Indiana Inc., Indianapolis, Ind.

[21] Appl. No.: 411,836

[22] Filed: Sep. 25, 1989

[51] Int. Cl.$^5$ ............................................. A61B 17/22
[52] U.S. Cl. .................................................... 606/127
[58] Field of Search ............... 606/127, 128, 198, 200; 604/107, 96, 104; 128/898, 756, 759, 757, 758

[56] References Cited

U.S. PATENT DOCUMENTS

| | | | |
|---|---|---|---|
| 4,447,227 | 5/1984 | Kotsanis | 604/101 |
| 4,927,426 | 5/1990 | Dretler | 606/128 |

FOREIGN PATENT DOCUMENTS

| | | | |
|---|---|---|---|
| 2739589 | 3/1979 | Fed. Rep. of Germany | 604/96 |
| 3545176 | 7/1987 | Fed. Rep. of Germany | 606/127 |

Primary Examiner—C. Fred Rosenbaum
Assistant Examiner—William W. Lewis
Attorney, Agent, or Firm—Woodard, Emhardt, Naughton, Moriarity & McNett

[57] ABSTRACT

A percutaneous catheter with encapsulating receptacle comprises a first catheter having a proximal and distal end, several struts attached to the distal end of the first catheter and extending distally therefrom in a cup-shaped form, a second, inner catheter received within the first, and a pocket-shaped sheath received between the several struts and opening in the distal direction, the sheath having a proximal portion secured to the distal end of the second, inner catheter, and a distal portion secured to the distal ends of the several struts, whereby rotation of the first catheter, relative the second catheter, twists and closes the distal end of the sheath. A third, outer catheter is also disclosed within which the first and second catheters, and associated struts and sheath, are receivable. Also disclosed is a method for positioning the catheter adjacent an object, or receiving the object within the sheath and enclosing the sheath about the object to facilitate treatment of the object.

23 Claims, 3 Drawing Sheets

PERCUTANEOUS CATHETER WITH ENCAPSULATING RECEPTACLE

BACKGROUND OF THE INVENTION

1. Field of the Invention:

The present invention relates to the field of medical devices for removing calculi, and particularly to such devices for use in percutaneous procedures.

2. Description of the Prior Art:

Instruments for removing calculi, for example, kidney and gallstones, without major surgery, are commonly of two general types. One takes the form of an expandable basket, and the other consists of miniaturized grasping forceps. Such instruments are typically inserted through endoscope passages and through naturally or artificially-formed body passages. One problem associated with both types of instruments lies in the possible injury to surrounding tissue as a grasped stone is extracted through the body passage or organ. Such dangers may be reduced by fragmenting the stone in situ by lithotripsy. However, such fragmentation may create additional problems if fragments remain and provide the nuclei for further stone development. During shattering, fragments can pass out of view, such as into lateral branches of the kidney cavity, and can thus be overlooked.

It has been known in the art that there are advantages in providing a means by which stone fragments produced in situ are contained in a confined area. For example, in U.S. Pat. No. 4,696,297, issued to Pleines, et al. on Sept. 29, 1987, there is described a method for encapsulating the stone fragments in a gel to prevent their escape. According to the Pleines procedure, a flowable gelatin solution is introduced into the body cavity so that the stone to be shattered is embedded therein. As a result of the cooling of the solution, a solid gel is formed in which the stone is enclosed. The stone is then shattered and the fragments remain within the gel to be thereafter collected and removed. The gel is then liquified and the gelatin solution also removed.

In U.S. Pat. No. 4,611,594, issued to Grayhack, et al. on Sept. 16, 1986, there is described a medical instrument for containment and removal of calculi. The Grayhack Patent discloses several embodiments for such an instrument. In one embodiment, a catheter has an expandable distal end within which a stone, held for example by a typical stone basket, can be drawn within and enclosed thereby. In a second embodiment, a catheter includes several struts which extend outwardly from the distal end, and a webbing is secured to and supported by the struts. The struts and webbing are normally positioned in an open configuration, but are forced closed when the catheter and struts are pulled into a second, outer catheter. In a third embodiment, the struts and supported webbing are secured to an inner catheter, and are normally maintained in a closed position. Guide wires are secured to another catheter and are operable to pull the struts and webbing outwardly into an open condition for receipt of a stone basket and contained stone. Similarly in a fourth embodiment, the struts and webbing are secured to an inner catheter and a control webbing is secured to an outer catheter to pull the normally closed struts into an open condition. In each of the embodiments described in the Grayhack, et al. Patent, the webbing is secured only to the supporting struts and the associated catheter, and forces are applied from externally of the webbing and struts to either push the normally open struts closed, or to pull open the normally closed struts.

Several catheter designs in the prior art have employed end balloons for encapsulating objects adjacent the tip of the catheter. Devices of this type are shown, for example, in U.S. Pat. Nos. 4,324,262, issued to Hall on Apr. 13, 1982; 4,469,100, issued to Hardwick on Sept. 4, 1984; and, 4,243,040 issued to Beecher on Jan. 6, 1981. Catheters having umbrella or parachute type configurations for collecting materials, as the catheters are drawn longitudinally, are disclosed in U.S. Pat. Nos. 3,472,230, issued to Fogarty on Oct. 14, 1969; and, 4,790,812 issued to Hawkins, Jr., et al. on Dec. 13, 1988.

SUMMARY OF THE INVENTION

Briefly describing one aspect of the present invention, there is provided a percutaneous catheter with encapsulating receptacle which includes a first catheter having a distal end, several struts having proximal ends secured to the distal end of the first catheter and extending axially therefrom, the struts in a normal, substantially untensioned condition defining a cup-shaped form opening in the distal direction, a second, inner catheter received within the first catheter, and a pocket-shaped sheath received between the several struts and opening in the distal direction, the sheath having a proximal portion secured to the distal end of the catheter and a distal portion secured to the distal ends of the several struts.

In an alternate embodiment, the foregoing first catheter is received within a third, outer catheter, the first and second catheters having a first, relatively rotated condition in which the struts and sheath are twisted and closed and received within the third catheter, and the first and second catheters having a second non-rotated condition in which the first and second catheters extend outwardly of the third catheter and the struts and sheath are in an open position.

A method for encapsulating an object by use of a percutaneous catheter is also disclosed herein.

It is an object of the present invention to provide a percutaneous catheter that includes a mechanism for encapsulating an object, particularly for treatment by dissolution or fragmentation.

It is another object of the present invention to provide an encapsulating catheter which is readily inserted and manipulated, requires only a small incision, creates minimal trauma to the treated organ, and for which the organ should be able to withstand repeated procedures. Use of this catheter will result in reduced time for the patient to be in the hospital and away from work.

It is a further object of the present invention to provide an encapsulating catheter useful in breaking up calculi by fragmentation methods, and which will reduce the time necessary to break up the calculi and will retain the stone fragments to permit collection of all of the fragments in a minimum amount of time.

A further object of the present invention is to provide an encapsulating, percutaneous catheter with which dissolution agents may be used, and by which potentially harmful effects to the body can be minimized or eliminated due to containment of the dissolution agent within the catheter.

Further objects and advantages of the present invention will become apparent from the description of the preferred embodiment which follows.

DESCRIPTION OF THE PREFERRED EMBODIMENT

Figure 1:
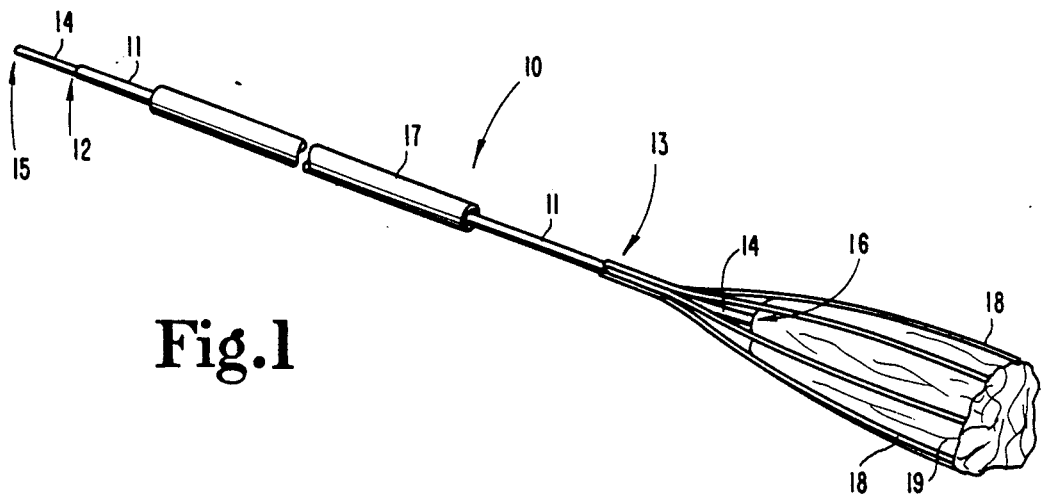
FIG. 1 is a perspective view of the percutaneous catheter with encapsulating receptacle according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides a percutaneous catheter with an encapsulating receptacle for the receipt therein of various calculi, such as gallstones or kidney stones. An advantage of this catheter is that the encapsulating receptacle provides a means for encasement, trapping and dissolution or breaking up (including contact shock wave, contact laser and mechanical crushing) of stones, particularly gallstones. Stones can be drawn into the open receptacle via a vacuum, forceps, or other types of grasping methods of devices. Large stones are then encapsulated by rotating the distal end of the webbing or sheath until this sheath is wound to a closed condition. The stone is then accessible from the catheter side to be dissolved (such as with methyl terbutyl ether), broken up or crushed.

By encapsulating the stone in the catheter sheath, harmful dissolution substances will be prevented from entering the gallbladder or body, thus preventing damage to the body tissues and eliminating the body's need to metabolize the substance (by absorption and exhalation), while also preventing potential hemolysis and acute duodenitis. Also, by encapsulating the stone in the catheter sheath prior to stone break-up (via contact shockwave, contact laser or mechanical crushing), the stone fragments will be prevented from being lost in the gallbladder, and thereafter potentially forming new stones. Although the apparatus and method are discussed herein in particular relationship to the gallbladder and gallstones, it will be appreciated that this is by way of illustration only, and the percutaneous catheter of the present invention is equally suited to use in other circumstances, such as those relating to kidney stones.

The advantages of the percutaneous catheter of the present invention are numerous. As for other percutaneous devices and procedures, the use of the present invention requires only a small incision, and there is reduced trauma to the patient. The time necessary to break up a stone is lessened given that the stone is trapped, thus eliminating the need to search repeatedly for the stone.

Referring in particular to the drawings, there is shown a percutaneous catheter with encapsulating receptacle constructed in accordance with a preferred embodiment of the present invention. The apparatus 10 includes a first catheter 11 having a proximal end 12 and a distal end 13. A second, inner catheter 14 is received within the catheter 11 and also includes a proximal end 15 and a distal end 16. Inner catheter 14 is slidable and rotatable relative to the primary catheter 11. The primary catheter 11 is slidably receivable within a third, outer catheter 17.

Figure 2:
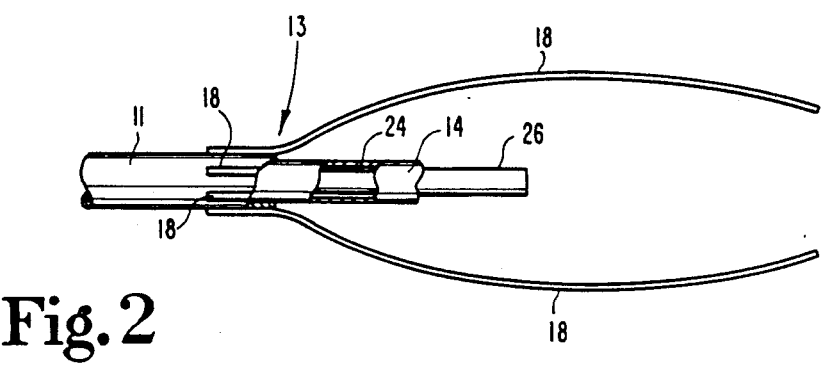
FIG. 2 is a partial, side elevational view of a portion of the present invention, particularly showing the attachment of the struts to the associated catheter.

Several struts 18 are secured to the distal end 13 of the primary catheter 11, and extend axially beyond the distal end of the catheter, as shown, for example in FIG. 2. These struts 18 are spaced about the periphery of the catheter 11 and are shaped and positioned to have a normal, substantially untensioned condition defining a cup-shaped form opening in the distal direction. The apparatus 10 preferably includes at least four struts, and in a preferred embodiment includes eight struts spaced about the circumference of catheter 11. Each of the struts in a normal, substantially untensioned condition, has an arcuate, concave shape facing inward toward the first catheter, as shown in the drawings.

The catheter 11 and struts 18 may be formed from a variety of materials suitable for use with the invention and providing the desired degree of flexibility and rigidity. For certain applications, the catheter 11 may constitute a relatively rigid cylinder of a biocompatible metal or plastic. In other applications, it is preferable to form the catheter 11 from a material that provides sufficient flexibility as to be directed through the body, and such materials are well known in the art. Similarly, the struts 18 are formed from biocompatible materials having the desired physical characteristics, and which are suitably securable to the catheter 11. In a preferred embodiment of the present invention, the distal end portion of the primary catheter 11 is metal, and the struts 18 are formed as metal struts which are welded to the distal end of the catheter 11.

Figure 7:
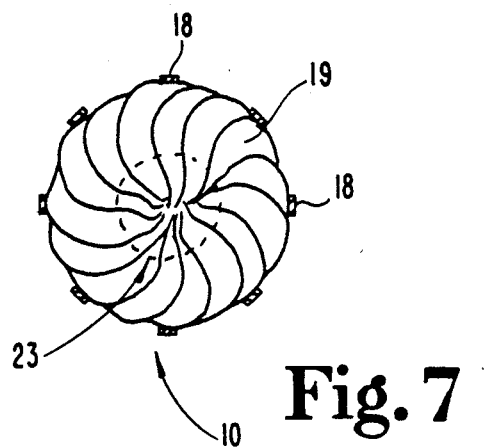
FIG. 7 is an end, cross-sectional view of the apparatus of the present invention, taken along the line 7—7 in FIG. 4 and looking in the direction of the arrows.

The struts are desirably formed as flat, elongated members having a generally rectangular cross-section with the shorter dimension lying in a radial position relative the first catheter (FIG. 7). This configuration for the struts 18 facilitates securement to the catheter 11 with the struts in the proper orientation, and also facilitates the desired bending and flexing of the struts as will be described hereafter.

Figure 3:
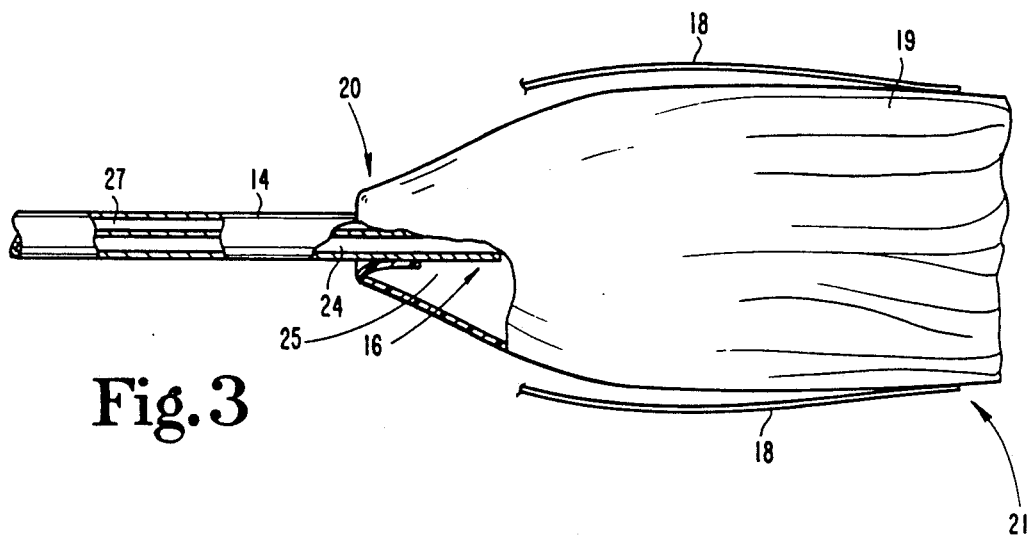
FIG. 3 is a partial, side elevational view of a portion of the invention, particularly showing the attachment of the sheath to the innermost catheter and to the struts.

A pocket-shaped sheath 19 is received between the several struts 18 and opens in the distal direction (FIG. 3). The sheath has a proximal portion 20 secured about the distal end of the inner catheter 14, and a distal portion 21 secured to the distal ends of the several struts 18. As shown particularly in FIG. 3, the sheath 19 in the preferred embodiment is folded over at the location of attachment, with the innermost, terminal portion being secured to the catheter 14. Also, it is preferable to have the distal end of the catheter 14 extend partially into the sheath interior to prevent the sheath from collapsing over the end of the catheter 14 and block its passageway. Attachment of the proximal and distal portions of sheath 19 at the respective locations may be accomplished in a variety of ways, such as by the use of suitable adhesives.

The inner catheter 14 and sheath 19 may be formed from a variety of suitable, biocompatible materials. Inner catheter 14 may be formed, for example, from various plastics well known in the art to be suitable for catheters, and may be either rigid or quite flexible. The flexible sheath 19 is preferably formed from a thin, flexible material which permits the sheath to be readily twisted for purposes hereafter described.

Figure 4:
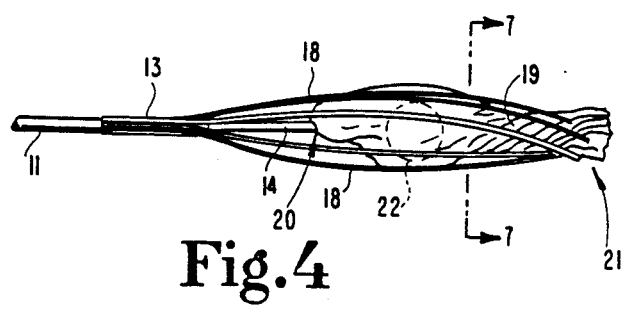
FIG. 4 is a partial, side elevational view showing the encapsulating receptacle and a calculus received therein.
Figure 5:
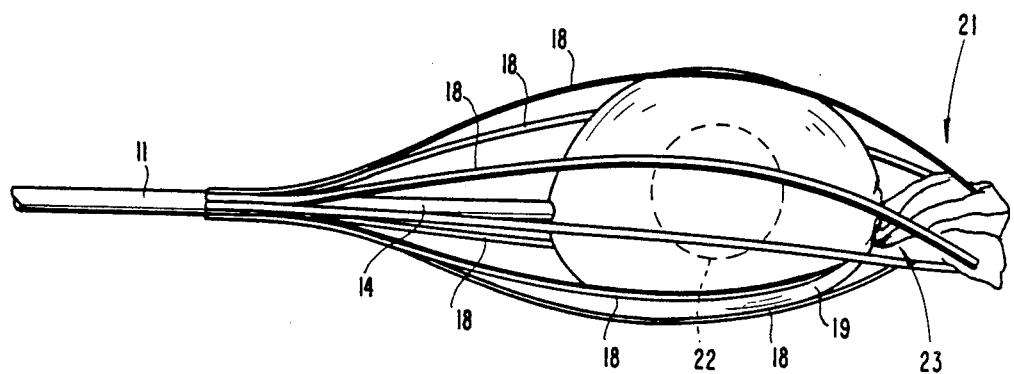
FIG. 5 is a partial, side elevational view similar to that of FIG. 4, with the difference being that the sheath is shown somewhat inflated as by the introduction of fluid under pressure.

Referring in particular to FIGS. 1, 4 and 5, the cooperation between the primary catheter 11 and inner catheter 14 is shown. In FIG. 1, the struts 18 and sheath 19 are shown in a normal, substantially untensioned condition with the struts and sheath defining a pocket facing in the distal direction. A calculus or stone 22 is shown received within the sheath 19 in FIGS. 4 and 5. With the stone 22 received within the sheath 19, the inner catheter 14 is rotated relative the primary catheter 11. This may of course be accomplished either by holding the outer catheter stationary and rotating the inner catheter, or holding the inner catheter stationary and rotating the outer catheter. The struts 18 will resist rotating, and as a result, the sheath 19 will twist and close at a location 23 adjacent the distal end 21. With appropriate selection and sizing of materials for the various described components, the resistance of struts 18 to the twisting action will permit the sheath 19 to be tightly twisted closed at 23. In this fashion, the stone 22 is fully encapsulated within the sheath 19 and the distal end of the sheath which is normally open in the untensioned condition (FIG. 1) is substantially or totally sealed off at 23 (FIG. 7). If desired, fluid under pressure may be introduced into the interior of the sheath 19 to inflate it, thus permitting the stone to move freely within the sheath when in the condition of FIG. 5.

Relative rotation of the primary catheter 11 and inner catheter 14 may be accomplished by suitable manipulation of the proximal ends 12 and 15, respectively. It will be appreciated that suitable, conventional handles members or connectors may be secured to the proximal ends of the catheters to facilitate manipulation of the components of the apparatus 10.

The inner catheter 14 includes a central lumen 24 which communicates with the interior 25 (FIG. 3) of the sheath 19. Various instruments, represented diagrammatically as 26 in FIG. 2, may be inserted through the lumen 24 into and/or beyond the interior 25 of the sheath. For example, grasping forceps could be extended through lumen 24 and beyond sheath 19 to initially pull a stone 22 into the sheath. Alternatively, scopes, lithotripsy devices, etc. could be extended through lumen 24. Alternatively, the device 10 could be passed through a separate, larger catheter along side of other devices such as a scope or lithotripsy device. In addition, fluids may be passed through lumen 24 either for passage out of the sheath 19 or for use within sheath 19. The admission of fluids through lumen 24 is particularly useful for the introduction of fluids to be used in acting upon a stone 22. As previously described, it is an advantage of the present invention that dissolution fluids such as methyl terbutyl ether may be introduced into the closed sheath of FIG. 5 to act upon the contained stoned without entry of the liquid into the surrounding body cavity.

The inner catheter 14 may be provided with multiple lumens, such as shown for example in FIG. 3. In addition to a lumen 24, the catheter may include a second lumen 27, or additional lumens. As is generally understood, the provision of multiple lumens can be useful to permit simultaneous use of the two or more lumens. For example, in the use of a dissolution fluid it may be desirable to introduce the fluid through a second lumen 27 and to withdraw the fluid and dissolved material through the lumen 24. As another example of the many uses for multiple lumens, it may be desirable to introduce a lithotripsy device through one lumen and to view the activity with a scope introduced through a second lumen.

Figure 6:
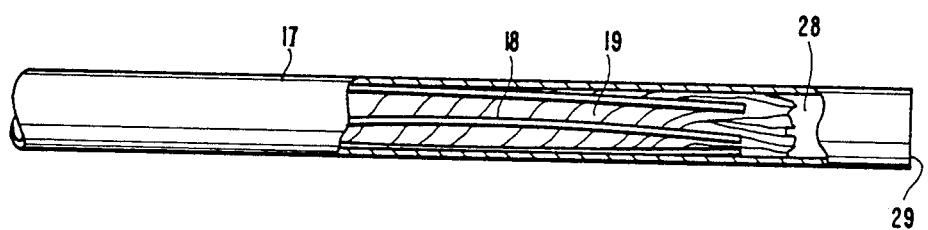
FIG. 6 is a partial, side view of the apparatus of FIG. 1, and particularly showing reception of the struts and sheath within the outermost catheter.

Referring in particular to FIG. 6, it is shown that the struts 18 and sheath 19 are receivable within the outer catheter 17. Without a stone 22 or other object received within the sheath, the sheath and struts may be collapsed into a minimal size that is conveniently receivable within the outer catheter 17. As shown in FIG. 1, the struts 18 and sheath 19 have a normally open position associated with the primary catheter 11 and inner catheter 14 being in an unrotated position relative one another. However, with the primary catheter 11 rotated relative the inner catheter 14 with no objects received within the sheath 19, the struts and sheath will collapse and twist into a generally cylindrical shape that is receivable within the lumen 28 of outer catheter 17, as shown in FIG. 6. While in this collapsed condition, the struts and sheath and associated catheters may be extended from or withdrawn into the outer catheter 17, which is particularly useful for introduction or retraction of the device from a body cavity, such as the interiors of the gallbladder or kidney.

It will be appreciated that the outer catheter 17 is conveniently used to introduce the contained components into the desired location within the body. Once in position, the primary catheter 11 and inner catheter 14 may be extended out of the distal end 29 of outer catheter 17, and thereafter the relative rotation of the catheters 11 and 14 will permit the struts and sheath to open into the position shown in FIG. 1. The outer catheter 17 is therefore desirably formed from a biocompatible material that has a flexibility sufficient for use of the apparatus 10 for a given application. For example, in certain instances, it will be desirable to have all of the components of apparatus 10 to be sufficiently flexible as to be directed along a path in the body to the site of the targeted calculus. Conversely, the unit may be conveniently retracted from the body cavity by collapsing the sheath and struts from the open condition of FIG. 1 to the compact condition of FIG. 6 and then withdrawing the inner components into the outer catheter 17.

In accordance with a method of the present invention, the described catheters 11 and 14, and associated struts and sheath, are positioned adjacent to a targeted object. The object is received within the sheath, and the primary and inner catheters are rotated relative one another to close the distal end of the sheath. To facilitate the capturing of the object within the sheath, an object-grasping device 26 may be extended through the central lumen of the inner catheter 14 to grasp the object and pull the object into the sheath.

In an alternate method, the catheters 11 and 14 are received within a third, outer catheter 17 when the struts 18 and sheath 19 are in the collapsed condition as shown in FIG. 6. The outer catheter 17 is then positioned adjacent the intended object, and the catheters 11 and 14 are extended out beyond the distal end of the catheter 17 and manipulated to capture the object. This capture may be the result of manipulation of the sheath and struts alone, or by the use of an object-grasping device extended through the lumen of the inner catheter 14. Once the object has been received within the encapsulating receptacle, various treatments may be performed on the object such as chemical dissolution or lithotripsy.

Passage of the overall apparatus into a desired body cavity may be accomplished by various methods. In one approach, a relatively larger catheter is passed into the body cavity by conventional techniques and the apparatus 10 is directed through this separate, larger catheter. In this approach, the invention may comprise simply the primary and inner catheters 11 and 14, or may also comprise the outer catheter 17. The separate, larger catheter may then also be used to pass other devices, such as scopes, etc., to the same body site.

Figure 8:
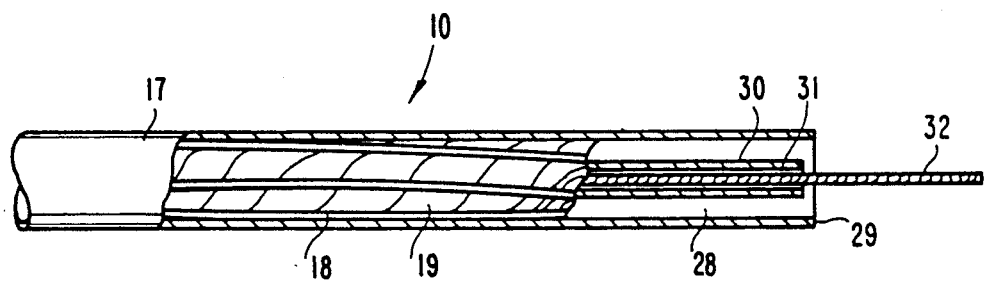
FIG. 8 is a partial, side view of the apparatus of FIG. 1, and particularly showing the struts and sheath in the collapsed condition and receiving therein a fourth catheter and a wire guide.

The present invention may alternately be directed percutaneously to the desired body cavity by means of a wire guide used in the following fashion. As shown in FIG. 8, a fourth catheter 30 is received through the lumen of interior catheter 14 and extends beyond the distal end of the sheath 19. In the collapsed condition, the sheath and struts close down on the catheter 30, but the central lumen 31 of the catheter provides a passageway for receipt of a wire guide 32. Absent the catheter 30, the sheath could sufficiently constrict as to prevent extension of a wire guide therethrough.

In the method of extending the unit into the body cavity, the unit may be used in conjunction with a wire guide 32 in accord with known techniques. The wire guide is directed to the target location within the body cavity in conventional fashion. The apparatus 10 is provided with a catheter 30 which is extended through the interior of inner catheter 14 and through the free or expanded sheath in the form as shown in FIG. 1. The sheath and struts are then collapsed through relative rotation of catheters 14 and 11. The wire guide 32 is then received within the lumen 31 of catheter 30 and the apparatus 10 is fed over the wire guide to the desired point within the body cavity. Once in position, the wire guide may be removed from catheter 30, and the catheter 30 may be removed from catheter 14 upon expansion of the sheath and struts in the manner previously described.

Figure 9:
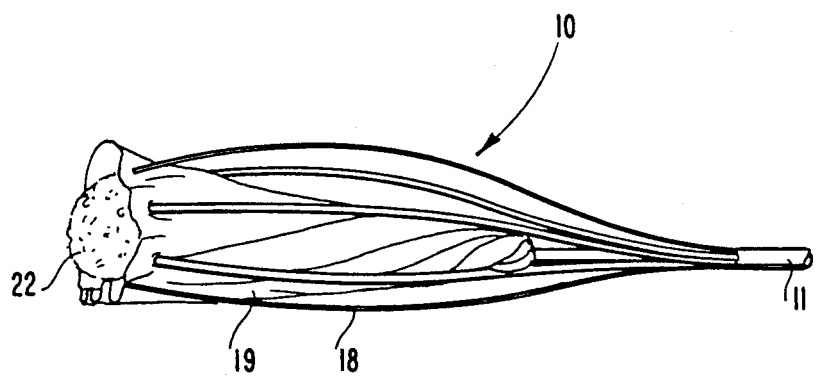
FIG. 9 is a partial, side elevational view of the present invention, showing the operation of the apparatus for the grasping of a calculi.

As indicated, it is a purpose and advantage of the present invention that the encapsulating receptacle, comprised of the sheath and supporting struts, can be used to capture and enclose a stone 22 or other object. In addition to the use of separate grasping devices extended through the lumen of the inner catheter 14, this capture can be accomplished simply by operation of the sheath and struts and associated structures. For example, as shown in FIG. 9, a calculi 22 may be grasped by the present invention by positioning the open end of the sheath 19 around the calculi and then rotating the inner catheter 14 relative the outer catheter 11. This relative rotation will cause the sheath 19 to partially twist and collapse, drawing the struts 18 inwardly and closing down on the calculi as shown. The calculi may be drawn further into the sheath by the application of suction within the sheath through the interior lumen of catheter 14, thus pulling the calculi into the sheath interior.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A percutaneous catheter with encapsulating receptacle which comprises:
    a first catheter having a proximal end and a distal end;
    several struts having proximal and distal ends, the proximal ends of said struts being secured to the distal end of said first catheter, said struts extending axially beyond the distal end of said first catheter, said struts in a normal, substantially untensioned condition defining a cup-shaped form opening in the distal direction;
    a second, inner catheter received within said first catheter, said second catheter having a proximal end and a distal end; and
    a pocket-shaped sheath received between said several struts and opening in the distal direction, said sheath having a proximal portion secured about the distal end of said second cathether, said sheath having a distal portion secured to the distal ends of said several struts,
    said sheath having a first condition in which said first catheter is non-rotated relative said second catheter, said struts are in a normal, substantially untensioned condition and said sheath defines a pocket-shaped opening, and said sheath having a second condition in which said first catheter is rotated relative said second catheter and the distal end of said sheath is twisted closed.

2. The invention of claim 1 in which each of said struts consists of a flat strip having a rectangular cross-section with the shorter dimension oriented in a direction radial to said first catheter.

3. The invention of claim 1 and which includes at least four struts.

4. The invention of claim 3 and which includes eight struts.

5. The invention of claim 1 in which each of said struts in a normal, substantially untensioned condition has an arcuate, concave shape facing inward toward said first catheter.

6. The invention of claim 5 in which each of said struts consists of a flat strip having a rectangular cross-section with the shorter dimension oriented in a direction radial to said first catheter.

7. The invention of claim 5 and which includes at least four struts.

8. The invention of claim 7 and which includes eight struts.

9. The invention of claim 8 in which each of said struts consists of a flat strip having a rectangular cross-section with the shorter dimension oriented in a direction radial to said first catheter.

10. The invention of claim 1 in which said sheath defines an interior and in which said second catheter defines a central lumen communicating with the interior of said sheath.

11. The invention of claim 1 and which further includes a third, outer catheter within which said first and second catheters are received, said third catheter including a proximal end and a distal end, the distal ends of said first and second catheters being received within said third catheter when in the second, rotated position with said struts and sheath twisted and closed, the distal ends of said first and second catheters extending outwardly of the distal end of said third catheter when in the first position with said struts and sheath being opened in the distal direction.

12. The invention of claim 11 in which each of said struts in a normal, substantially untensioned condition has an arcuate, concave shape facing inward toward said first catheter.

13. The invention of claim 12 in which each of said struts consists of a flat strip having a rectangular cross-section with the shorter dimension oriented in a direction radial to said first catheter.

14. The invention of claim 13 and which includes at least four struts.

15. The invention of claim 14 and which includes eight struts.

16. The invention of claim 15 in which each of said struts consists of a flat strip having a rectangular cross-section with the shorter dimension oriented in a direction radial to said first catheter.

17. A method for encapsulating an object which comprises the steps of:
 a. providing an encapsulating receptacle which includes a first catheter having a proximal end and a distal end, several struts having proximal ends secured to the distal end of the first catheter and also having distal ends, the struts extending axially beyond the distal end of the first catheter, the struts in a normal, substantially untensioned condition defining a cup-shaped form opening in the distal direction, a second, inner catheter received within the first catheter, the second catheter having a proximal end and a distal end, and a pocket-shaped sheath received between the several struts and opening in the distal direction, the sheath having a proximal portion secured about the distal end of the second catheter, the sheath having a distal portion secured to the distal ends of the several struts;
 b. positioning the encapsulating receptacle adjacent to the object;
 c. receiving the object within the sheath of said receptacle; and
 d. rotating the first catheter relative the second catheter to close the distal end of the sheath.

18. The method of claim 17 in which the second catheter defines a central lumen communicating with the interior of the sheath, said receiving of step c. comprising extending an object-grasping device through the central lumen of the second catheter, grasping the object, and pulling the object into the sheath.

19. The method of claim 18 in which said positioning of step b. comprises inserting the first and second catheters through a third, outer catheter, the distal ends of said first and second catheters being received within the third catheter when in the first, rotated position with the struts and sheath twisted and closed and received within the third catheter, the distal ends of the first and second catheters extending outwardly of the distal end of the third catheter when in the second position with the struts and sheath being opened in the distal direction.

20. The method of claim 19 in which the second catheter defines a central lumen communicating with the interior of the sheath, said receiving of step c. comprising extending an object-grasping device through the central lumen of the second catheter, grasping the object, and pulling the object into the sheath.

21. The method of claim 20 in which the second catheter defines a central lumen communicating with the interior of the sheath, and which further includes the step e. of passing material through the central lumen.

22. The method of claim 21 in which step e. comprises passing material through the central lumen and into the sheath to act upon the object.

23. The method of claim 22 in which step e. comprises passing the object from the sheath through the central lumen.

* * * * *